United States Patent [19]

Herting et al.

[11] Patent Number: 5,208,034
[45] Date of Patent: May 4, 1993

[54] TETRAAMIDES AND METHOD FOR IMPROVING FEED UTILIZATION

[75] Inventors: David C. Herting, Carter County; Alan W. White, Kingsport, both of Tenn.

[73] Assignee: Eastman Kodak Company, Rochester, N.Y.

[21] Appl. No.: 935,496

[22] Filed: Aug. 25, 1992

Related U.S. Application Data

[62] Division of Ser. No. 280,083, Dec. 5, 1988, Pat. No. 5,141,749.

[51] Int. Cl.⁵ ............................................. A23K 1/165
[52] U.S. Cl. ................................... 424/442; 424/439; 514/625; 514/626
[58] Field of Search ............... 424/442, 439; 514/625, 514/626

[56] References Cited

U.S. PATENT DOCUMENTS 3,492,398  1/1970  Marco ............................ 424/438

OTHER PUBLICATIONS

H. Maeda et al., *Bull. Chem. Soc. Jpn.*, 56, 3073 (1983).

*Primary Examiner*—Thurman K. Page
*Assistant Examiner*—D. Gabrielle Phelan
*Attorney, Agent, or Firm*—Mark A. Montgomery; William P. Heath, Jr.; Thomas R. Savitsky

[57] ABSTRACT

Disclosed are novel tetraamide compounds and intermediates therefor which are useful in methods for improving feed conversion and/or weight gain in animals such as chickens.

10 Claims, No Drawings

TETRAAMIDES AND METHOD FOR IMPROVING FEED UTILIZATION

This is a divisional application of copending application Ser. No. 07/280,083 filed on Dec. 5, 1988, now U.S. Pat. No. 5,141,749.

FIELD OF INVENTION

The present invention relates to novel compounds and methods for improving feed conversion and/or weight gain in animals.

BACKGROUND OF THE INVENTION

As is well known, there is a need to develop methods that increase or optimize the productivity of animals to enhance food production. Not only does the producer benefit by lower costs of production but the consumer benefits ultimately from increased supplies of meat and animal products at a lower cost.

For approximately the last 35 years, antibiotics such as penicillin, the tetracyclines, and bacitracin have enabled benefits to both producer and consumer by enhancing growth and/or improving feed conversion in animals, most effectively in poultry and swine.

Benefits from incorporating antibiotics into animal feeds are usually attributed to their minimizing the deleterious effects of pathogenic microorganisms in the gastrointestinal tract of the host. Evidence for the induction of antibiotic-resistant microorganisms and concern for their possible transfer to and infection of humans have generated broad searches for compounds that will improve animal performance without substantially impinging on human health concerns.

SUMMARY OF THE INVENTION

We have now discovered certain tetraamides as hereinafter described which have beneficial effects on improving animal performance.

More specifically, the present invention is directed to a method for increasing the efficiency of feed utilization by animals which comprises administering the said animals an effective feed utilization efficiency increasing amount of a tetraamide compound of the formula

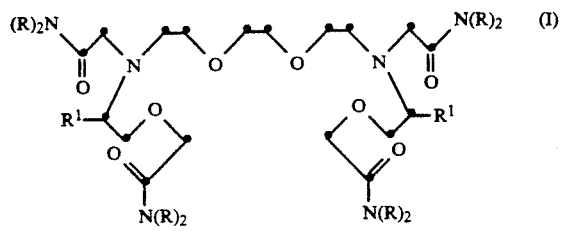

wherein each R is, independently, an alkyl group of 1 to 6 carbon atoms; and each $R^1$ is, independently, an alkyl group of 1 to 6 carbons or hydrogen.

The present invention is also directed to the novel compounds of Formula I.

The present invention also includes certain intermediate compounds used to prepare the compounds of Formula I. Such intermediates are of the formula:

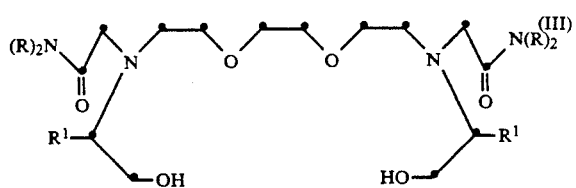

wherein each R and $R^1$ are, independently, as described above.

The present invention is also directed to a method for promoting the growth of meat-producing animals comprising administering an effective growth promoting amount of a compound of Formula I to meat-producing animals.

The present invention is also directed to an animal feed composition comprising standard animal feed in admixture with from about 20 parts per million (ppm) to about 1,000 ppm of the total amount of the ultimate diet formulation of a compound of Formula I.

DETAILED DESCRIPTION OF THE INVENTION

As used herein, the term "animals" excludes humans and refers to any animal grown in the art of animal husbandry for use by humans for food, clothing and the like; such animals include meat-producing, egg-producing, and milk-producing animals; for example, ruminants such as cattle, sheep and goats and nonruminants such as swine and poultry. The term "meat-producing animals" refers to any animal grown in the art of animal husbandry for use of its meat as food. The term "egg-producing" animals refers to any animal grown in the art of animal husbandry for use of its eggs as food. The term "milk-producing animal" refers to any animal grown in the art for use of its milk as food. The term "standard animal feed" refers to that feed that can be used in the animal husbandry field and is suitable to be fed to animals to supply part or all of the animals' nutrient requirements. The term "effective feed utilization efficiency increasing amount" refers to that amount of a compound of Formula I that, when administered to animals, will increase the feed utilization efficiency of such animals, without any significant adverse side effect, as compared to untreated animals. It is contemplated that such amount of Compound I will also result in other beneficial effects as a result of the increased feed conversion efficiency such as increased efficiency of egg production, milk production, wool production, and the like. The term "effective growth promoting amount" refers to that amount of a compound of Formula I that will, when administered to meat-producing animals, promote the growth of, increase the growth rate of, and/or increase the weight gain of such meat-producing animals, without any significant adverse side effect, as compared to untreated animals.

It is to be understood that the methods for feed utilization efficiency improvement and growth promotion will in many circumstances overlap. However, the two types of methods are recognized in the art as being different in many instances. As a result, for example, some treated animals may demonstrate increased feed conversion efficiency without concomitant growth promotion. This may be desired in some situations, for example, in poultry such as chickens wherein the primary purpose for growing the chickens is for egg production. A typical effective feed utilization efficiency increasing amount of a compound of Formula I is about 2 to about 100 milligrams (mg) per kilogram (kg) of body weight per day; a more preferred range is about 5 to about 50 mg per kg of body weight per day. Typical effective growth promoting amounts of the compound of Formula I are about the same as the effective feed utilization efficiency increasing amounts.

As appreciated in the art, effective amounts of a compound of Formula I for use in the present invention will vary somewhat depending upon the particular species of animal, age, growth conditions such as temperature and type of feed, and the like. For any particular case, the exact or optimal effective amount to be administered can be determined by conventional dose titration techniques. Also, it is contemplated that a mixture of two or more of the compounds of Formula I can be used in the methods of the present invention.

For either of the two methods of the present invention nonruminant animals are preferred, especially poultry. Of the preferred poultry, the most preferred is chickens.

In the feed conversion efficiency improvement method of the present invention it is preferred that the feed conversion efficiency is improved at least about 1.0%, more preferred is at least about 2.0%, as compared to untreated animals. In the growth promotion method of the present invention it is preferred that treated animals have at least about a 2.0%, more preferred is at least about a 4.0%, increase in weight gain as compared to untreated animals.

The compositions of the present invention can be formulated as end use feed mixes or can be formulated as feed premixes, supplements or concentrates. The compositions of the present invention can optionally contain one or more other physiologically acceptable additives which can be inert or act as adjuvants. Such additives include, but are not limited to, nutrients and carriers such as amino acids, organic acids, soybean meal, ground corn, ground corn cobs, corn oil, barley, wheat or other edible feed grade material, mineral or vitamin mixtures; innocuous diluents such as an alcohol, a glycol, or molasses; feed preservatives; antibiotics; coccidiostats; and the like. The compound of Formula I, whether administered via water or feed, can be used in combination with other treatments, whether for the same or a different purpose, such as use of drugs and hormone implants.

The form of administration of a compound of Formula I to the animal is not crucial, and alternative forms for administering the tetraamide compound may be employed. For instance, the compound can be incorporated into tablets, drenches, salt blocks, paste, boluses, or capsules and doped to the animals. Formulation of the compounds in such dosage forms can be accomplished by means of methods well known in the veterinary pharmaceutical art. Each individual dosage unit should contain a quantity of the compound which has a direct relation to the proper daily dose for the animal to be treated, as discussed above.

The compositions of the present invention contain an amount of the compound of Formula I in order for the animals to consume an amount of said compound that will be effective in improving the animals feed conversion and/or promoting the growth of said animal. The compositions of the present invention are diet formulations comprising standard animal feed for meat-producing animals in admixture with from about 20 ppm to about 1,000 ppm of the total amount of the ultimate diet formulation of the compound of Formula I; a preferred amount of said compound is from about 50 ppm to about 500 ppm; and a most preferred amount of said compound is from about 100 ppm to about 300 ppm. Orally administering compositions with the above noted concentration of the compound of Formula I will result in the treated animals receiving an effective amount of the compound of Formula I. Therefore a method for orally administering such compositions to animals is also within the scope of the present invention. The exact amount desired to be in the diet formulation will vary depending upon age, weight, health and species of animal, the specific compound of Formula I or mixture of compound of Formula I, other components in the diet formulation, and the like.

In the compound of Formula I it is preferred that R is an alkyl group of 3-5 carbons. It is most preferred that R is isobutyl. It is preferred that $R^1$ is an alkyl group of 1-3 carbons. It is most preferred that $R^1$ is ethyl. The compound of Formula I can be prepared by the route outlined in the scheme below.

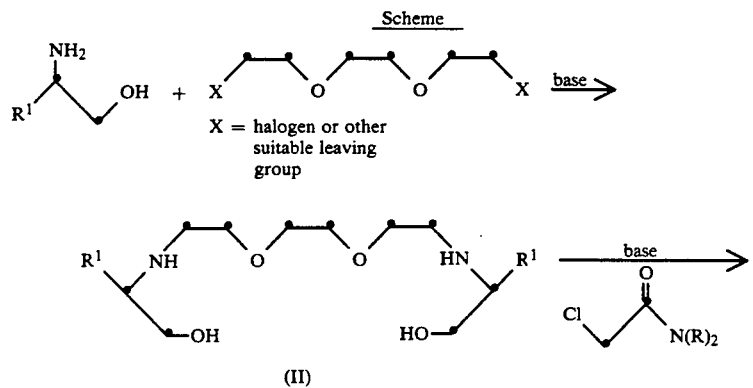

Scheme

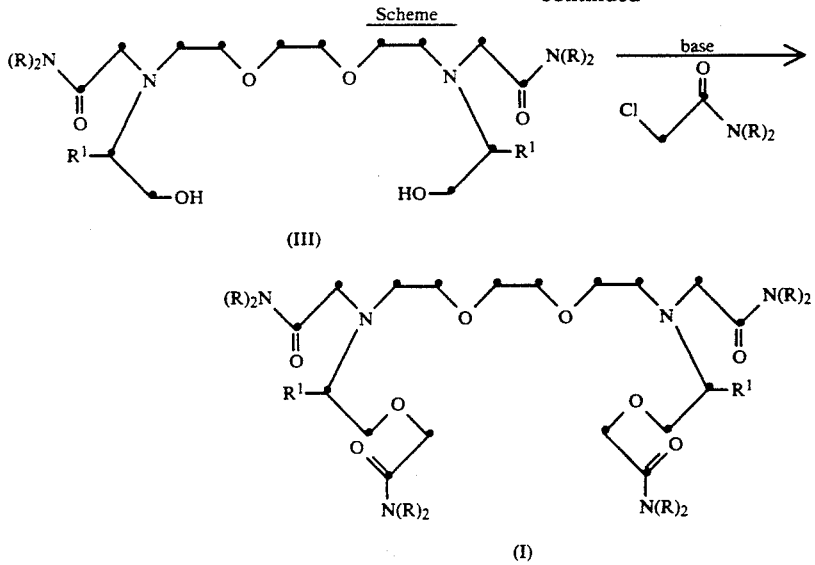

This scheme shows how (I) can be prepared. The starting materials for this scheme are either commercially available or can be prepared by techniques well known in the art. A number of variations are possible, including choice of base, solvent and reaction conditions. Typical bases include, for example, triethylamine, diethylisopropylamine, and sodium carbonate; typical solvents include, for example, 1,2-dimethoxyethane, dimethylformamide, and dimethylsulfoxide; typical reaction conditions include, for example, a temperature of 50° to 100° C. for a reaction period of 1 to 24 hours. It is also possible that the last two steps in the above scheme can be combined into one operation. The chloroamide used in steps 2 and 3 can be prepared from the corresponding disubstituted amine and chloroacetyl chloride in the presence of base. In addition, other haloamides such as the appropriate bromoamide or iodoamide can be used in place of the chloroamide in steps 2 and 3.

The salts of the compounds of this invention can be derived from physiologically acceptable acids. Such physiologically acceptable acids include inorganic acids, e.g., hydrochloric acid, nitric acid, phosphoric acid, sulfuric acid, hydrobromic acid, hydroiodic acid, nitrous acid, phosphorous acid, and the like, as well as organic acids, such as aliphatic mono- or dicarboxylic acids, phenyl-substituted alkanecarboxylic acids, hydroxyalkanecarboxylic acids or alkanedicarboxylic acids, aromatic acids, aliphatic or aromatic sulfonic acids, and the like.

Physiologically acceptable salts of these acids include therefore, for example, the sulfate, pryosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propionate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, beta-hydroxybutyrate, glycollate, malate, tartrate, methanesulfonate, propanesulfonate, naphthalene-1-sulfonate, naphthalene-2-sulfonate, and the like.

The salts of the compound of the present invention can be prepared according to procedures commonly employed for the preparation of amine salts. For example, the free base form of a compound of Formula I is dissolved in a suitable solvent, and an aqueous or organic solution of the desired acid is added. The salts can be isolated by filtration and recrystallization or by evaporation of the solvent and purification.

EXAMPLES

The following examples are provided in order to further illustrate the present invention and should not be construed as limiting the invention in any way.

EXAMPLE I

Preparation of Compound II wherein $R^1$=Ethyl

Diol II ($R^1$=ethyl) was prepared by a procedure similar to that described in the literature (H. Maeda et al., *Bulletin of the Chemical Society of Japan*, 56, 3073 (1983)). Sodium carbonate (8.0 g, 75.0 mmol), R-(-)2-amino-1-butanol (44.5 g, 50.0 mmol, 46.0 mL) and 1,8-dichloro-3,6-dioxaoctane (9.35 g, 50.0 mmol, 7.8 mL) were combined and heated to 120° C. for 24 hours. When the reaction mixture had cooled, it was filtered. The filtrate was concentrated and distilled using a Kugelrohr apparatus (0.05 mm, 175°-200° C.). The distilled material contained about 5% starting material as indicated by gas chromatography. The viscous oil was triturated with ether/hexanes to give a waxy white solid. The yield was 8.9 g (61%). The NMR spectrum, infrared spectrum and field desorption mass spectrum (FDMS) confirmed the structure of the desired product.

EXAMPLE II

Preparation of Compound III wherein R=Isobutyl and $R^1$=Ethyl

A mixture of Compound II ($R^1$=ethyl), 2-chloro-N,N-diisobutylacetamide (2.05 g, 0.01 mol), triethylamine (1.3 mL) and dimethoxyethane (10 mL) was heated to reflux under an argon atmosphere. After 24 hours the reaction was shown to be incomplete. More dimethoxyethane (10 mL), chloroamide as described above (2.05 g) and triethylamine (1.3 mL) were added. The mixture was again heated to reflux. After 17 hours the solvent was removed, and the residue was partitioned between methylene chloride and 1N HCl. The acidic layer was made basic and extracted with ethyl acetate. The ethyl acetate layer was dried and concentrated to a light yellow oil (0.94 g). The NMR spectrum, infrared spectrum and the mass spectrum (field desorption) of the yellow oil were consistent with the desired structure.

EXAMPLE III

Preparation of Compound I wherein R=Isobutyl, and $R^1$=Ethyl

Diamidediol Compound III (R=isobutyl, $R^1$=ethyl) (0.45 g, 0.0008 mol) was combined with 2-chloro-N,N-diisobutylacetamide (0.36 g, 0.0018 mol), sodium hydride (60% in mineral oil, 75 mg) and dimethoxyethane (10 mL) and heated to reflux for two hours. After the reaction mixture had cooled, one drop of water was added, and the solvent was removed. The residue was partitioned between methylene chloride and 1N HCl. The organic layer was washed with aqueous sodium carbonate, and the solvent was evaporated to give 0.84 g of an oil. This crude material was chromatographed through alumina (neutral) with heptane and then ether. Because little alumina was used, the product eluted from the column in the early fractions with heptane as the eluant. This material was shown to be >95% pure by NMR, infrared and mass spectrum.

EXAMPLE IV

Birds arriving before two days of age were given water and the untreated control diet ad libitum until they were two days old. Approximately 10% extra birds were ordered to enable discard of the runts and giants. Birds were distributed by weight as evenly as possible to provide four pens of ten birds each on each treatment. Distribution of pens in the brooders was random, but restricted to ensure at least one pen in the upper two tiers, at least one pen in the middle two tiers, and at least one pen in the lower two tiers for each treatment. Brooder temperatures were approximately 95° F. throughout the trial. The compounds of Formula (I) were dissolved in ethanol prior to premixing with the basal diet. Water and feed were provided ad libitum. Feed/gain calculations include weight gained by birds dying during the second week of the experiment. The specific diets, other test conditions and results are shown in Tables 1-4.

TABLE 1

UNTREATED CONTROL DIET
Composition of Semi-Purified Diet for Broiler Chicks

| Ingredient | Amount (%) |
|---|---|
| Sucrose | 62.55 |
| Isolated Soy Protein (Pro-Fam S-901)[a] | 26.90 |
| Salt Mixture (DCH SYN MIN)[b] | 4.35 |
| Refined Soybean Oil[c] | 4.50 |
| Glycine | 0.30 |
| Choline Chloride | 0.20 |
| Inositol | 0.10 |
| Vitamin Premix (DCH SYN VIT)[d] | 0.50 |
| Dl-Methionine | 0.60 |

TABLE 1-continued

UNTREATED CONTROL DIET
Composition of Semi-Purified Diet for Broiler Chicks

| Ingredient | Amount (%) |
|---|---|
| | 100.00 |

[a]Grain Processing Corporation
[b]See Table 2
[c]Crisco or equivalent
[d]See Table 3

TABLE 2

Composition of Salt Mixture (DCH SYN MIN)

| Ingredient | gm |
|---|---|
| Calcium Carbonate ($CaCO_3$) | 1050.0 |
| Potassium Phosphate, Dibasic ($K_2HPO_4$) | 462.0 |
| Sodium Phosphate, Dibasic ($Na_2HPO_4$) | 330.0 |
| Calcium Phosphate, Monobasic [$Ca(H_2PO_4)_2 \cdot H_2O$] | 500.0 |
| Sodium Chloride (NaCl) | 264.0 |
| Magnesium Sulfate ($MgSO_4$) | 161.2 |
| Manganous Sulfate ($MnSO_4 \cdot H_2O$) | 19.8 |
| Potassium Iodide (KI) | 0.07 |
| Zinc Carbonate ($ZnCO_3$) | 6.6 |
| Cupric Sulfate ($CuSO_4 \cdot 5H_2O$) | 0.79 |
| Ferric Citrate | 10.56 |
| Sodium Molybdate ($Na_2MoO_4 \cdot 2H_2O$) | 0 0.4 |
| Sodium Selenite ($Na_2SeO_3$) | 0.073 |
| | 2805.493 |

TABLE 3

Composition of Vitamin Premix (DCH SYN VIT)

| Ingredient | Amount |
|---|---|
| Vitamin A (Rovimix, 650,000 IU/g) | 500.0 mg |
| Vitamin $D_3$ (1,000,000 IU/g) | 12.0 mg |
| Vitamin E (Eastman 700 IU/g) | 714.0 mg |
| 2-Methyl-1,4-naphthoquinone | 20.0 mg |
| Thiamine · HCl | 200.0 mg |
| Riboflavin | 320.0 mg |
| d-Calcium pantothenate | 400.0 mg |
| Niacin | 1200.0 mg |
| Vitamin $B_{12}$ (0.1% in mannitol) | 800.0 mg |
| Biotin | 4.0 mg |
| Pyridoxine · HCl | 120.0 mg |
| Folic acid | 80.0 mg |
| p-Aminobenzoic acid | 2000.0 mg |
| Glucose | 193.63 g |

TABLE 4

Effect of the Compound of EXAMPLE III (R = isobutyl, $R^1$ = ethyl) on Chick Growth and Feed Efficiency

| Diet[a] | Level of Treatment (mg/kg)[b] | Chick Weight[c] (g ± std. dev.) | Feed Conversion (g feed/ g gain) |
|---|---|---|---|
| Untreated control | 0 | 318.3 ± 41.9 | 1.15 |
| Untreated Control plus Penicillin G (as sodium salt) | 55 | 354.6 ± 45.6[d] | 1.15 |
| Untreated control plus Compound I (R = isobutyl, $R^1$ = ethyl) | 55 | 321.3 ± 41.3 | 1.13 |
| Untreated control Plus Compound I (R = isobutyl, $R^1$ = ethyl) | 220 | 335.2 ± 31.6[e] | 1.12 |

[a]All diets based on Untreated Control Diet. Diets stored at 4° C. Treatments were premixed with, and added at the expense of, the rest of the dietary components.
[b]Expressed as active ingredient.
[c]At 15 days old. The last 13 days were on treatment. The chicks were Marek's vaccinated, White Mountain X Hubbard cockerels. Average initial weight was 51.4 g.
[d]Growth enhanced compared with untreated controls ($p < 0.05$).
[e]Growth enhanced compared with untreated controls (p is approximately 0.053).

The invention has been described in detail with particular reference to preferred embodiments thereof, but it will be understood that variations and modifications can be effected within the spirit and scope of the invention.

We claim:

1. A compound of the formula:

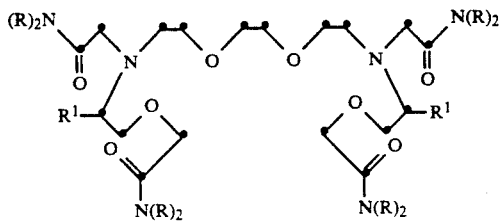

wherein each R is, independently, an alkyl group of 1 to 6 carbon atoms and each R$^1$ is, independently, an alkyl group of 1-6 carbons or hydrogen, 2. The compound of claim 1 wherein each R is an alkyl group of 3-5 carbon atoms and each R$^1$ is an alkyl group of 1-3 carbon atoms.

3. The compound of claim 1 wherein each R is isobutyl and each R$^1$ is ethyl.

4. A composition comprising standard animal feed in admixture with from about 20 ppm to about 1,000 ppm of the total amount of the ultimate composition of a tetraamide compound of the formula:

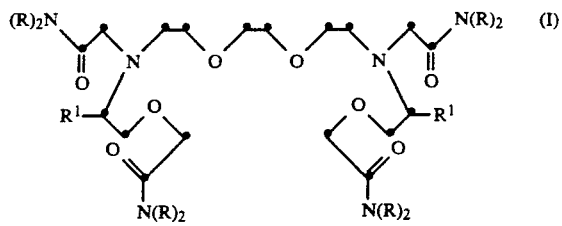

wherein each R is independently, an alkyl group of 1 to 6 carbon atoms and each R$^1$ is, independently, an alkyl group of 1-6 carbons or hydrogen, or the physiologically acceptable salts thereof.

5. The composition of claim 4 wherein the amount of said tetraamide compound is about 50 ppm to about 500 ppm of the ultimate diet formulation.

6. The composition of claim 4 wherein each R is an alkyl group of 3-5 carbon atoms and each R$^1$ is an alkyl group of 1-3 carbon atoms.

7. The composition of claim 4 wherein each R is isobutyl and each R$^1$ is ethyl.

8. A compound of the formula:

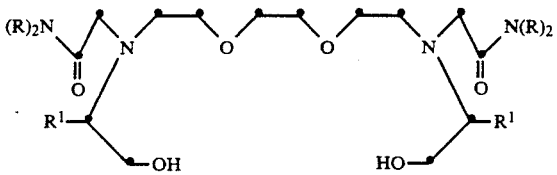

wherein each R is independently, an alkyl group of 1 to 6 carbon atoms and each R$^1$ is, independently, an alkyl group of 1-6 carbons or hydrogen, or the physiologically acceptable salts thereof.

9. The compound of claim 8 wherein each R is an alkyl group of 3-5 carbon atoms and each R$^1$ is an alkyl group of 1-3 carbon atoms.

10. The compound of claim 8 wherein each R is isobutyl and each R$^1$ is ethyl.

* * * * *

UNITED STATES PATENT AND TRADEMARK OFFICE
CERTIFICATE OF CORRECTION

PATENT NO. : 5,208,034
DATED : May 4, 1993
INVENTOR(S) : David C. Herting, Alan W. White It is certified that error appears in the above-identified patent and that said Letters Patent is hereby corrected as shown below:

Column 9, line 27 after hydrogen, insert ---or the physiologically acceptable salts thereof.---

Signed and Sealed this

Twenty-sixth Day of April, 1994

Attest:

BRUCE LEHMAN

Attesting Officer      Commissioner of Patents and Trademarks